(12) United States Patent
Bittner et al.

(10) Patent No.: US 9,566,590 B2
(45) Date of Patent: Feb. 14, 2017

(54) AMINE AND DIAMINE COMPOUNDS AND THEIR USE FOR INVERSE FROTH FLOTATION OF SILICATE FROM IRON ORE

(75) Inventors: Christian Bittner, Bensheim (DE); Joerg Nieberle, Wachenheim (DE); Bernhard Ulrich Von Vacano, Mannheim (DE); Alexsandro Berger, Rosenheim (DE); Roland Boehn, Maxdorf (DE); Guenter Oetter, Frankenthal (DE)

(73) Assignee: BASF SE, Ludwigshafen (DE)

( * ) Notice: Subject to any disclaimer, the term of this patent is extended or adjusted under 35 U.S.C. 154(b) by 503 days.

(21) Appl. No.: 14/110,633

(22) PCT Filed: Apr. 10, 2012

(86) PCT No.: PCT/EP2012/056398
§ 371 (c)(1),
(2), (4) Date: Oct. 8, 2013

(87) PCT Pub. No.: WO2012/139986
PCT Pub. Date: Oct. 18, 2012

(65) Prior Publication Data
US 2014/0021104 A1    Jan. 23, 2014

Related U.S. Application Data

(60) Provisional application No. 61/474,758, filed on Apr. 13, 2011.

(30) Foreign Application Priority Data

Apr. 13, 2011  (EP) .................................... 11162183

(51) Int. Cl.
| | | |
|---|---|---|
| *B03D 1/02* | (2006.01) | |
| *B03D 1/01* | (2006.01) | |
| *C07C 217/08* | (2006.01) | |
| *B03D 1/016* | (2006.01) | |
| *C07C 29/34* | (2006.01) | |

(52) U.S. Cl.
CPC . *B03D 1/02* (2013.01); *B03D 1/01* (2013.01); *B03D 1/016* (2013.01); *C07C 29/34* (2013.01); *C07C 217/08* (2013.01); *B03D 2201/02* (2013.01); *B03D 2201/04* (2013.01); *B03D 2201/06* (2013.01); *B03D 2203/04* (2013.01)

(58) Field of Classification Search
None
See application file for complete search history.

(56) References Cited

U.S. PATENT DOCUMENTS

| | | |
|---|---|---|
| 2,629,494 A | 2/1953 | Brown et al. |
| 3,363,758 A | 1/1968 | Cronberg et al. |
| 4,319,987 A | 3/1982 | Shaw et al. |
| 4,422,928 A | 12/1983 | McGlothlin et al. |
| 5,540,337 A | 7/1996 | Riggs et al. |
| 6,076,682 A * | 6/2000 | Gustafsson ............... B03D 1/02 209/166 |
| 6,114,585 A | 9/2000 | Daly et al. |
| 6,331,648 B1 | 12/2001 | Daly et al. |
| 7,371,716 B2 * | 5/2008 | Ruland .................. A01N 25/30 510/342 |
| 8,701,892 B2 * | 4/2014 | Gustafsson ............... B03D 1/01 209/166 |
| 2005/0215452 A1 | 9/2005 | Ruland et al. |
| 2006/0009368 A1 | 1/2006 | Noerenberg et al. |
| 2009/0114879 A1 | 5/2009 | Hellsten et al. |

FOREIGN PATENT DOCUMENTS

| | | |
|---|---|---|
| CA | 1100239 | 4/1981 |
| WO | WO 2007/107502 A1 | 9/2007 |
| WO | WO 2008/077849 A1 | 7/2008 |

OTHER PUBLICATIONS

International Preliminary Report on Patentability and Written Opinion issued Oct. 24, 2013 in PCT/EP2012/056398.
International Search Report and Written Opinion issued Dec. 11, 2012 in PCT/EP2012/056398.
Srdjan M. Bulatovic, "Handbook of Flotation Reagents: Chemistry, Theory and Practice, Ether Amines", Flotation of Sulfide Ores, Jan. 1, 2007, Elsevier, XP55033529, 3 pages.
A. C. C Araujo, et al., "Reagents in iron ores flotation", Minerals Engineering , vol. 18, No. 2, Feb. 1, 2005, XP027815644, pp. 219-224.
R. M. Papini, et al "Cationic flotation of iron ores: amine characterization and performance", Minerals and metallurgical Processing, vol. 18, No. 1, Jan. 1, 2001, XP009090087, pp. 5-9.

(Continued)

*Primary Examiner* — Thomas M Lithgow
(74) *Attorney, Agent, or Firm* — Oblon, McClelland, Maier & Neustadt, L.L.P.

(57) ABSTRACT

The invention relates to a process for enriching an iron mineral from a silicate containing iron ore by inverse flotation comprising the addition of a collector or collector composition comprising at least one of the compounds of formulae RO—X—$NH_2$ (Ia); RO—X—$NH_3^+Y^-$ (Ib); RO—X—NH—Z—$NH_2$ (IIa); and RO—X—NH—Z—$NH_3^+Y^-$ (IIb), in which X is a linear or branched aliphatic alkylene group containing 2 to 6 carbon atoms; Z is a linear or branched aliphatic alkylene group containing 2 to 6 carbon atoms; Y− is an anion; and R is an aliphatic group of the formula (I) $C_5H_{11}CH(C_3H_7)CH_2$— (I) wherein the $C_5H_{11}$ moeity of the aliphatic group of the formula (I) comprises 70 to 99% by weight n-$C_5H_{11}$—, and 1 to 30% by weight $C_2H_5CH(CH_3)CH_2$— and/or $CH_3CH(CH_3)CH_2CH_2$—.

| | |
|---|---|
| RO—X—$NH_2$ | (Ia) |
| RO—X—$NH_3^+Y^-$ | (Ib) |
| RO—X—NH—Z—$NH_2$ | (IIa) |
| RO—X—NH—Z—$NH_3^+Y^-$ | (IIb) |
| $C_5H_{11}CH(C_3H_7)CH_2$— | (I) |

12 Claims, No Drawings

(56) References Cited

OTHER PUBLICATIONS

R. M. F. Lima, et al., "Influence of the degree of neutralization of amines in iron ore reverse flotation", Información Tecnológica, vol. 13, No. 5, Jan. 1, 2002, XP009128945, pp. 3-7 (with English abstract) Additional References sheet(s) attached.

* cited by examiner

AMINE AND DIAMINE COMPOUNDS AND THEIR USE FOR INVERSE FROTH FLOTATION OF SILICATE FROM IRON ORE

The present invention relates to a process for enriching an iron mineral from a silicate-containing iron ore by carrying out an inverse ore flotation process using alkyl ether amines and/or alkyl ether diamines. The invention also relates to novel ether amines and alkyl ether diamines and formulations containing the same.

Removal of $SiO_2$ from different ores by froth flotation and hydrophobic amines is a well known process and is described for example by S. R. Rao in *Surface Chemistry of Froth Flotation, Volume 1 and 2*, $2^{nd}$ edition, Kluwer Academic/Plenum Publishers, New York 2004. The negatively charged silicate can be hydrophobized using suitable amines. Injection of air in a flotation cell leads to formation of hydrophobic gas bubbles, which can transport the hydrophobized silicate particle to the top of the flotation cell. At the top a froth, which can be stabilized by a suitable frother, collects the silicate particles. Finally, the froth will be removed from the surface and the enriched mineral is left at the bottom of the flotation cell.

In the case of iron ore, pure material is necessary to make high quality steel. Therefore the iron mineral can be enriched from a silicate-containing iron ore by inverse flotation. This kind of froth is carried out in the presence of a depressing agent for the iron mineral and collecting agent, which can contain hydrophobic amines, for instance alkyl ether amines and/or alkyl ether diamines.

In U.S. Pat. No. 2,629,494 (Attapulgus Minerals+Chemicals Corp., publication date 24 Feb. 1953) protonated hydrophobic amines like tetradecylamine acetate are described to remove silicate from iron oxide in the presence of starch as depressing agent.

U.S. Pat. No. 3,363,758 (Ashland Oil and Refining Company, publication date 16 Jan. 1968) relates to a froth flotation process for separating silica from an ore employing a water dispersible aliphatic ether diamine of the formula R—O—CH2CH(R")CH2NHCH2CH(R")CH2-NH2 in which R is an aliphatic radical having between one and 13 carbon atoms and R" is a hydrogen atom or a methyl group.

In CA1100239 (Akzona, Inc., publication date 28 Apr. 1981) alkyl ether diamines of the structure alkoxy-$CH_2CH_2CH_2$—NH—$CH_2CH_2CH_2$—$NH_2$ for removal of silicate from iron ore were described. Alkoxy unit should contain 6 to 22 carbon atoms and could be linear or branched. The disadvantage of linear alkoxy moieties is that the collector starts to crystallize with time. Additional solvent or a heating unit would be necessary to enable a liquid dosage.

Exxon Research and Engineering Co described in U.S. Pat. No. 4,319,987 (publication date 16 Mar. 1982) the use of alkoxy-$CH_2CH_2CH_2$—$NH_2$ for removal of silicate from iron ore. Alkoxy unit should contain 8-10 carbon atoms and should be branched.

U.S. Pat. No. 4,422,928 (Exxon Research and Engineering, publication date 27 Dec. 1983) reveals a froth flotation process for separating silica from iron ore employing a liquid aliphatic ether amine of the formula R—O—($R^1$—O)$_z$—$CH_2$—$CH_2$—$CH_2$—$NH_2$ in which R is an aliphatic methyl branched radical having nine carbon atoms, $R_1$ is ethyl or propyl and z is an integer of from zero to 10.

In U.S. Pat. No. 6,076,682 (AKZO NOBEL NV, publication date 20 Jun. 2000) combinations out of ether amines and ether polyamines for inverse iron ore flotation were described. Especially structures alkoxy-$CH_2CH_2CH_2$—$NH_2$ with alkoxy consisting out of 8 to 12 carbon atoms and alkoxy-$CH_2CH_2CH_2$—NH—$CH_2CH_2CH_2$—$NH_2$ with alkoxy consisting out of 8 to 14 carbon atoms were preferred.

WO 2008/077849 (AKZO NOBEL NV, publication date 3 Jul. 2008) describes a collecting composition for use in enriching an iron mineral from a silicate containing iron or containing coarse silicates having a $K_{80}$ value of at least 110 µm by reverse flotation of the ore. The composition contains a mixture of at least one diamine of the formula $R^1$O-A-NH(CH$_2$)$_n$NH2, in which $R^1$ is a straight or branched hydrocarbyl group which 12 to 15 carbon atoms, A is a group —$CH_2CHXCH_2$—, in which X is hydrogen or a hydroxyl group; at least one amine of the formula $R^2$(O-A)$_x$-NH2, in which $R^2$ is a straight or branched hydrocarbyl group with 12 to 24 carbon atoms, x=0 or 1, and A is as defined before; and at least one diamine of the formula $R^3$(O-A)$_y$-NH(CH$_2$)$_n$NH$_2$, in which $R^3$ is a straight or branched hydrocarbyl group with 16 to 24 carbon atoms, y=0 or 1, and A is as defined before. Included in the lists of possible groups for each of $R^1$ and $R^2$ is methyl branched C13 alkyl (isotridecyl).

Despite a significant number of proposed structures in inverse iron ore flotation more selective compounds are needed because quality of ore has been decreasing. With higher $SiO_2$ content in the ore a selective removal of silicate is more difficult than in the past with ores of higher quality. Loss of iron ore in the flotation process should be avoided and silicate content should be decreased to a very low level especially for direct reduction processes (DRI-pellets). Therefore it is an objective of the present invention to find collectors which are useful for enriching an iron mineral that achieve this objective, especially for difficult iron ores containing high silicate content. It would be desirable to provide suitable flotation collectors and processes of selective removal of silicate from iron ore which overcome the aforementioned disadvantages. Furthermore, it would be desirable to provide flotation collectors which can be conveniently employed in flotation processes. It is particularly desirable for such floatation collectors to be in a liquid form.

According to the present invention we provide a process for enriching an iron mineral from a silicate containing iron ore by inverse flotation comprising the addition of a collector or collector composition comprising at least one of the compounds of formulae

  RO—X—$NH_2$ (Ia);

  RO—X—$NH_3^+Y^-$ (Ib);

  RO—X—NH—Z—$NH_2$ (IIa); and

  RO—X—NH—Z—$NH_3^+Y^-$ (IIb), in which
X is an aliphatic alkylene group containing 2 to 6 carbon atoms;
Z is an aliphatic alkylene group containing 2 to 6 carbon atoms;
$Y^-$ is an anion; and
R is an aliphatic group of the formula (I)

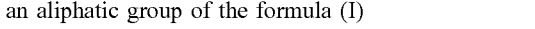  $C_5H_{11}CH(C_3H_7)CH_2$— (I)

wherein the $C_5H_{11}$ moeity of the aliphatic group of the formula (I) comprises
70 to 99% by weight n-$C_5H_{11}$—, and
1 to 30% by weight $C_2H_5CH(CH_3)CH_2$— and/or $CH_3CH(CH_3)CH_2CH_2$—.

The $C_3H_7$ moiety of formula (I) may be branched or linear but preferably is n-$C_3H_7$.

The X and Z aliphatic alkylene groups may each independently be linear or branched when containing 3 to 6 carbon atoms.

In accordance with the present invention any of the compounds of formulae (Ia), (Ib), (IIa) or (IIb) provide improved results in enriching the iron material. Preference may be given to use a combination of these compounds. For instance an alkyl ether amine compound (Ia) may be used in combination with a protonated alkyl ether amine compound (Ib). Alternatively an alkyl ether diamine compound (IIa) may be used in combination with a protonated alkyl ether diamine compound (IIb). It may also be desirable to use a combination of all four compounds of formulae (Ia), (Ib), (IIa), and (IIb). Thus these compounds or combinations thereof used in the process according to the present invention show a much better selective removal of silicate compared to the commercially available or other known alkyl ether amines or alkyl ether diamines.

In a preferred form X is an aliphatic alkylene group containing between 2 and 4 carbon atoms and especially three carbon atoms. It particularly preferred alkylene group has the structure —$CH_2CH_2CH_2$—.

Similarly in a preferred form Z is an aliphatic alkylene group containing between 2 and 4 carbon atoms and especially three carbon atoms. It particularly preferred alkylene group has the structure —$CH_2CH_2CH_2$—.

The anion $Y^-$ may be any suitable anion including a carboxylate, sulphate, sulphonate, chloride, bromide, iodide, fluoride, nitrate, phosphate etc. Preferably the anion is a carboxylate particularly an aliphatic or olefinic carboxylate of between 1 and 6 carbon atoms. More preferably the carboxylate is an aliphatic carboxylate of between 1 and 3 carbon atoms such as $HCO_2^-$, $CH_3CO_2^-$, $CH_3CH_2CO_2^-$, $CH_3CO_2^-$ is especially preferred.

The R group of compounds of formulae (Ia), (Ib), (IIa), and/or (IIb) may suitably be an aliphatic Guerbet-$C_{10}H_{21}$— group with average branching degree larger than 1. Preferably the mean degree of branching is between 1.01 and 1.60.

By Guerbet $C_{10}H_{21}$— group we mean that the corresponding alcohol $C_{10}H_{21}$—OH has been derived by dimerisation of a C5 aldehyde or a C5 alcohol, or example as given in US 2005215452.

The degree of branching is defined as the number of methyl groups in one molecule of R group minus 1. The average degree of branching is the statistical mean of the degree of branching of the molecules of a sample. The mean number of methyl groups in the molecules of a sample can easily be determined by $^1$H-NMR spectroscopy. For this purpose, the signal area corresponding to the methyl protons in the $^1$H-NMR spectrum of a sample is divided by three and then divided by the signal area of the methylene protons of the $CH_2O$—X group divided by two.

In one preferred form of the present invention any of the compounds of formulae (Ia), (Ib), (IIa) or (IIb) or combination thereof may be used in conjunction with at least one of compounds of formulae R'O—X—$NH_2$ (Ic);

R'O—X—$NH_3^+Y^-$ (Id);

R'O—X—NH—Z—$NH_2$ (IIc); and

R'O—X—NH—Z—$NH_3^+Y^-$ (IId), in which
X, Y and Z are each independently selected from the aforementioned definitions; and R' is an aliphatic $C_{13}H_{27}$— group and/or an aliphatic $C_{15}H_{31}$— group each with average branching degree ranging from 0.1 to 0.9 preferably between 0.3 and 0.7. The degree of branching is as defined previously.

In another preferred form of the present invention any of the compounds of formulae (Ia), (Ib), (IIa) or (IIb) or combination thereof may be used in conjunction with at least one of compounds of formulae R"O—X—$NH_2$ (Ie);

R"O—X—$NH_3^+Y^-$ (If);

R"O—X—NH—Z—$NH_2$ (IIe); and

R"O—X—NH—Z—$NH_3^+Y^-$ (IIf), in which
X, Y and Z are each independently selected from the aforementioned definitions; and R" is a linear aliphatic $C_{12}H_{25}$— group and/or a linear aliphatic $C_{14}H_{29}$— group.

The invention also relates to novel compounds of formulae

RO—X—$NH_2$ (Ia);

RO—X—$NH_3^+Y^-$ (Ib);

RO—X—NH—Z—$NH_2$ (IIa);

RO—X—NH—Z—$NH_3^+Y^-$ (IIb), in which X, Y, Z, and R are each independently selected from the aforementioned definitions.

Compounds of formula (Ia), (Ic), and (Ie) may be prepared by firstly reacting an alcohol ROH, R'OH or R"OH respectively with an ethylenically unsaturated nitrile containing between 3 and 6 carbon atoms to provide an alkyl ether nitrile. The R, R' and R" groups respectively are as defined previously. Suitable ethylenically unsaturated nitriles include acrylonitrile, methacrylonitrile, ethacrylonitrile, 2-n-propylacrylonitrile, 2-iso-propylacrylonitrile, 2-methyl-1-butenenitrile, 3-methyl-1-butenenitrile, 2,2-dimethyl-1-butenenitrile, 2,3-dimethyl-1-butenenitrile, 2-ethyl-1-butenenitrile, 3-ethyl-1-butenenitrile, 2-methyl-1-butenenitrile, 3-methyl-1-butenenitrile, 2,3-dimethyl-1-butenenitrile, 2-ethyl-1-butenenitrile, 1-pentenenitrile, 2-methyl-1-pentenenitrile, 3-methyl-1-pentenenitrile, 4-methyl-1-pentenenitrile. Preferably the ethylenically unsaturated nitrile would contain three carbon atoms i.e. acrylonitrile. It may be desirable to carry out this step in the presence of a base and a polar solvent. Typically the base may be an alkali metal alkoxide, preferably an alkali metal ethoxide or alkali metal methoxide, especially sodium methoxide. The ethylenically unsaturated nitrile may be added in an equivalent molar quantity to the alcohol. Usually the ethylenically unsaturated nitrile could also be added in a stoichiometric excess in order to ensure that all of the alcohol is reacted. Often the molar ratio of the ethylenically unsaturated nitrile to the alcohol can be above 1:1 and up to 10:1, preferably from 1.5:1 to 5:1, more desirably between 1:1 and 2:1.

The alcohol ROH may be obtained commercially from BASF or prepared according to the teaching of US2005215452 (BASF AG, publication date 29 Sep. 2005). Typically the alcohol may be produced by dimerisation of slightly branched aldehyde containing five carbon atoms using the aldol reaction followed by hydrogenation. Preferably the alcohol will have a mean branching degree ranging from 1.01 to 1.60.

The alcohol R'OH may be obtained commercially from BASF. Typically the alcohol is a C13 or C15 oxo alcohol, for example available from BASF. Desirably these alcohols may be obtained by the hydroformylation of C12 or C14 alpha olefin respectively to form the corresponding C13 or C15 aldehyde followed by hydrogenation to form the corresponding alcohol, preferably having a mean branching degree of between 0.3 and 0.7.

The alcohol R"OH may be any linear fatty alcohol with 12 and/or 14 carbon atoms.

It may be desirable to combine the ethylenically unsaturated nitrile with the alcohol already containing the base over a period of between 5 minutes and 75 minutes or more, preferably between 30 minutes and 60 minutes. It may be desirable to control the rate of combining the nitrile with the alcohol in order to ensure an optimum temperature is achieved. The reaction temperature may be between 10° C. and 60° C. It may be desirable to control the temperature such that it does not exceed 50° C. The reaction time may be over a period of at least 5 minutes and as long as 24 hours. Typically the reaction will be at least 5 minutes and often as much as 10 hours or more. At the end of the reaction it may be desirable to remove the excess ethylenically unsaturated nitrile by conventional means, for example by evaporation under vacuum. Suitably the ethylenically a saturated nitrile may be removed under vacuum with a reduced pressure of between 15 mbar and 100 mbar at an elevated temperature of between 30° C. and 60° C. for a period of between 30 minutes and 180 minutes and optionally at an increased temperature of at least 65° C. and up to 85° C. Optionally it may be desirable to use a resin to remove any trace amounts of the nitrile. Desirably the resulting alkyl ether nitrile should have a purity of at least 90% and often at least 95%.

In a second step of the process the nitrile group of the alkyl ether nitrile of step one is reduced to the corresponding amine. This can be achieved by any conventional process for the reduction of nitriles to amines. Desirably the alkyl ether nitrile should be reacted with hydrogen in the presence of a suitable catalyst. An example of a suitable catalyst includes Raney-Cobalt. This may be carried out in the presence of a suitable aprotic solvent such as tetrahydrofuran.

Typically the reaction may be carried out at elevated temperatures, for instance at least 80° C., desirably at least 90° C., and possibly up to 140° C. or more. Preferably the reaction would be carried out at temperatures of between 100° C. and 130° C. In addition to elevated temperatures it may often be desirable to carry out process under increased pressure usually of at least 40 bar or more, for instance at least 45 bar. It may often be desirable to increase the pressure to even higher levels for instance up to 350 bar or higher, for instance between 250 bar and 300 bar. At the end of the reaction it may usually be desirable to remove the catalyst. This can be done by conventional filtration means.

Desirably the resulting alkyl ether amine should have a purity of at least 85% and often at least 89% or 90% or higher.

Compounds of formula (Ia) may be prepared also by the following process. In a first step an alcohol ROH in which the R group is as defined previously can suitably be reacted with 1 eq of alkylene oxide like ethylene oxide, propylene oxide, 1,-2-butylene oxide, 2,3-butylene oxide, 1,2-pentene oxide and/or 1,2-hexene oxide. Therefore alcohol ROH is mixed with a base like sodium hydroxide, potassium hydroxide or cesium hydroxide or aqueous solution out of it and reaction water is removed under reduced vacuum (15 to 100 mbar) at elevated temperature (80-120° C.) for suitable time. This could last between 0.5 and 3 hours. Reaction vessel is then flushed several times with nitrogen and heated to 100-160° C. Alkylene oxide is added in such a way that reaction temperature does not exceed 180° C. Optionally base can be neutralized with an acid (for example acetic acid) and resulting salt can be removed by simple filtration. Reaction leads to a mixture of showing a molecular weight distribution with an average alkoxylation degree of 1. Alkoxylation reaction can also be catalyzed by amines like imidazol or tertiary amines or double metal catalysts.

In a second step product from reaction before can be mixed with a suitable catalyst optionally in presence of an aprotic solvent like tetrahydrofurane. Reaction vessel is flushed several times with nitrogen in order to remove air. Afterwards ammonia (1-200 eq) and hydrogen (4-200 eq) are added up to a pressure of 50 bar. Reaction is heated under stirring to 200° C. Pressure should be kept below 280 bar. Further hydrogen is added (in case of pressure drop) and stirred over a period up to 24 h. Reaction is cooled to 40° C., gas is removed and vessel flushed several times with nitrogen. Catalyst can be removed by filtration and solvent can be removed under vacuum. Conversion of alcohol group into a primary amino group is at least 85% or even higher.

The compounds of formulae (Ib) (Id) and (If) may conveniently be prepared by addition of an acidic compound to the corresponding alkyl ether amine of formulae (Ia), (Ic), or (Ie). The acid the compound will protonate the amine group and then the negatively charged acid radical will form the negatively charged $Y^-$ component. The acidic compound may be any suitable acid, for instance acids whose radicals are selected from the group consisting of carboxylate, sulphate, sulphonate, chloride, bromide, iodide, fluoride, nitrate, and phosphate. Preferably the acid is a carboxylic acid, particularly an aliphatic or olefinic carboxylic acid having between one and six carbon atoms. More preferably a carboxylic acid is an aliphatic carboxylic acid having between one and three carbon atoms i.e. formic acid, acetic acid or propionic acid. Acetic acid is preferred.

The acidic compound may be added in a molar equivalence to the alkyl ether amine compound of formula (Ia). It may be desirable to add a lesser amount of the acidic compound which will result in partial protonation and therefore result in a mixture of the protonated compound of formula (Ib) and the corresponding alkyl ether amine compound of formula (Ia). It may also be desirable to add a greater amount of the acidic compound resulting in a stoichiometric excess of the acidic compound. Typically the ratio of acidic compound to alkyl ether amine may be between 1:10 and 1.5:1, especially between 1:7 and 1:1.

The acidic compound may be added over a period of time between one minute and 45 minutes to the alkyl ether amine, for instance between five minutes and 30 minutes. The resulting compound of formulae (Ib), (Id), or (If) respectively desirably will form as a homogenous solution which will remain clear and liquid during storage.

The alkyl ether diamines of formulae (IIa), (IIc) and (IId) may be synthesised by reacting the respective alkyl ether amine of formulae (Ia), (Ic) or (Ie) with an ethylenically unsaturated nitrile containing between 3 and 6 carbon atoms to provide an alkyl ether amino alkyl nitrile. Suitable ethylenically unsaturated nitriles include acrylonitrile, methacrylonitrile, ethacrylonitrile, 2-n-propylacrylonitrile, 2-iso-propylacrylonitrile, 2-methyl-1-butenenitrile, 3-methyl-1-butenenitrile, 2,2-dimethyl-1-butenenitrile, 2,3-dimethyl-1-butenenitrile, 2-ethyl-1-butenenitrile, 3-ethyl-1- butenenitrile, 2-methyl-1-butenenitrile, 3-methyl-1-butenenitrile, 2,3-dimethyl-1-butenenitrile, 2-ethyl-1-butenenitrile, 1-pentenenitrile, 2-methyl-1-pentenenitrile, 3-methyl-1-pentenenitrile, 4-methyl-1-pentenenitrile. Preferably the ethylenically unsaturated nitrile would contain three carbon atoms i.e. acrylonitrile.

The ethylenically unsaturated nitrile may be added in an equivalent molar quantity to the alkyl ether amine. Usually the ethylenically unsaturated nitrile could also be added in a stoichiometric excess in order to ensure that all of the alkyl ether amine is reacted. Often the molar ratio of the ethylenically unsaturated nitrile to the amine can be above 1:1 and up to 10:1, preferably from 1.5:1 to 5:1, more desirably between 1:1 and 2:1.

It may be desirable to combine the ethylenically unsaturated nitrile with the alkyl ether amine over a period of between 5 minutes and 75 minutes or more, preferably between 10 minutes and 45 minutes. It may be desirable to control the rate of combining the nitrile with the alcohol in order to ensure an optimum temperature is achieved. The reaction temperature may be between 10° C. and 60° C. It may be desirable to control the temperature such that it does not exceed 50° C. The reaction time may be over a period of at least 5 minutes and as long as 24 hours. Typically the reaction will be at least 5 minutes and often as much as 10 hours or more. At the end of the reaction it may be desirable to remove the excess ethylenically unsaturated nitrile by conventional means, for example by evaporation under vacuum. Suitably the ethylenically a saturated nitrile may be removed under vacuum with a reduced pressure of between 15 mbar and 100 mbar at an elevated temperature of between 30° C. and 60° C. for a period of between 30 minutes and 180 minutes and optionally at an increased temperature of at least 65° C. and up to 85° C. Optionally it may be desirable to use a resin to remove any trace amounts of the nitrile. Desirably the resulting alkyl ether amino alkyl nitrile should have a purity of at least 55% and often at least 60%

In a second step of the process the nitrile group of the alkyl ether amino alkyl nitrile of step one is reduced to the corresponding amine. This can be achieved by any conventional process for the reduction of nitriles to amines. Desirably the alkyl ether amino alkyl nitrile should be reacted with hydrogen in the presence of a suitable catalyst. An example of suitable catalysts includes Raney-Cobalt. This may be carried out in the presence of a suitable aprotic solvent such as tetrahydrofuran.

Typically the reaction may be carried out at elevated temperatures, for instance at least 80° C., desirably at least 90° C., and possibly up to 140° C. or more. Preferably the reaction would be carried out at temperatures of between 100° C. and 130° C. In addition to elevated temperatures it may often be desirable to carry out process under increased pressure usually of at least 40 bar or more, for instance at least 45 bar. It may often be desirable to increase the pressure to even higher levels for instance up to 350 bar or higher, for instance between 250 bar and 300 bar. At the end of the reaction it may usually be desirable to remove the catalyst. This can be done by conventional filtration means.

Desirably the resulting alkyl ether diamine should have a purity of at least 55% and often at least 60% or higher.

In an alternative process for producing the aforementioned alkyl ether diamines the respective corresponding alkyl ether amine can be reacted with a C2-6 alkylene oxide in a similar way as described above for formula (Ia) in order to produce this time the corresponding alkyl ether amino alcohol.

The compounds of formulae (IIb), (IId), or (IIf) may conveniently be prepared by addition of an acidic compound to the corresponding alkyl ether diamines of formula (IIa), (IIc) or (IIe). The acid the compound will protonate the amine group and then the negatively charged acid radical will form the negatively charged $Y^-$ component. The acidic compound may be any suitable acid, for instance acids whose radicals are selected from the group consisting of carboxylate, sulphate, sulphonate, chloride, bromide, iodide, fluoride, nitrate, and phosphate. Preferably the acid is a carboxylic acid, particularly an aliphatic or olefinic carboxylic acid having between one and six carbon atoms. More preferably a carboxylic acid is an aliphatic carboxylic acid having between one and three carbon atoms i.e. formic acid, acetic acid or propionic acid. Acetic acid is preferred.

The acidic compound may be added in a molar equivalence to the corresponding alkyl ether diamine compound of formula (IIa), (IIc) or (IIe). It may be desirable to add a lesser amount of the acidic compound which will result in partial protonation and therefore result in a mixture of the respective protonated compound of formula (IIb), (IId), or (IIf) and the corresponding alkyl ether diamine compound of formula (IIa), (IIc), or (IIe). It may also be desirable to add a greater amount of the acidic compound resulting in a stoichiometric excess of the acidic compound. Typically the ratio of acidic compound to alkyl ether diamine may be between 1:25 and 1.5:1, especially between 1:20 and 1:1.

The acidic compound may be added over a period of time between one minute and 45 minutes to the alkyl ether amine, for instance between five minutes and 30 minutes. The resulting compound of formula (IIb), (IId), or (IIf) desirably will form as a homogenous solution which will remain clear and liquid during storage.

The present invention also relates to the use of at least one of the compounds of formulae (Ia), (Ib), (IIa), (IIb) combined with at least one of the compounds of formulae (Ic), (Id), (Ie), (If), (IIc), (IId), (IIe) and/or (IIf) as flotation collectors for enriching an iron mineral from a silicate-containing iron ore.

For instance an alkyl ether amine compound (Ia) may be used in combination with the corresponding protonated alkyl ether amine compound (Ib), (Id) and/or (If). Alternatively an alkyl ether diamine compound (IIa) may be used in combination with the corresponding protonated alkyl ether diamine compound (IIb), (Id) and/or (If). It may also be desirable to use a combination of at least one compound of from all of formulae (Ia), (Ib), (IIa), and (IIb).

A preferred combination of compounds for use as collectors includes at least one compound of formulae (Ia), (Ib), (IIa), and/or (IIb) in combination with at least one compound of formulae (Ic), (Id), (IIc), and/or (IId).

Another preferred combination of compounds for use as collectors includes at least one compound of formulae (Ia), (Ib), (IIa), and/or (IIb) in combination with at least one compound of formulae (Ie), (If), (IIe), and/or (IIf).

The invention further relates to compositions suitable for use in enriching an iron mineral from a silicate-containing iron ore comprising of at least one of the compounds of formulae (Ia), (Ib), (Ic), (Id). Compositions comprising at least one compound according to at least one of formulae (Ia), (Ib), (IIa), and/or (IIb) combined with at least one compound according to at least one of formulae (Ie), (If), (IIa), (IIb), (IIc), (IId), (IIe) and/or (IIf) are preferred. One more preferred composition comprises at least one compound of formulae (Ia), (Ib), (IIa), and/or (IIb) in combination with at least one compound of formulae (Ic), (Id), (IIc), and/or (IId). Another more preferred composition comprises at least one compound of formulae (Ia), (Ib), (IIa), and/or (IIb) in combination with at least one compound of formulae (Ie), (If), (IIe), and/or (IIf).

The use of said composition as collecting formulations for enriching an iron mineral from a silicate-containing iron ore is also claimed.

When the compounds of the invention or formulations containing them are used as collectors or in collector formulations in an inverse flotation process a much better selection removal of silicate is achieved by comparison to commercially available or other known alkyl ether amines or other known collectors. The present invention provides improved removal of silicate without suffering an increased loss of the iron mineral. In fact the collectors of the present invention enable a higher proportion of the iron to be retained and a higher proportion of the silicate to be removed.

In the process according to the invention for enriching an iron mineral from a silicate containing iron ore by inverse flotation conventional inverse flotation plant equipment may be used. In general the iron ore can be combined with water or suitable aqueous liquid and mixed using mechanical mixing means to form a homogenous slurry. The flotation process is normally carried out in one or more flotation cells. The collector would normally be introduced into the slurry in the flotation cell. Typically the collector will condition the dispersed iron ore of the slurry. A suitable period of conditioning will tend to be at least one minute and sometimes as much as 10 or 15 minutes. Following the conditioning period air would tend to be injected into the base of the flotation cell and the air bubbles so formed would tend to rise to the surface and generate a froth on the surface. The injection an air may be continued until no more froth is formed, which may be for at least one minute and as much as 15 or 20 minutes. The froth can be collected and removed. In some cases it may be desirable to further treat the residual slurry again in a similar manner at least once for instance between 4 and 6 treatments. Nevertheless, it will generally be unnecessary to further treat the residual slurry again.

The flotation process may be performed in a conventional pH range. may be in the range of between 5 and 12, such as 9 and 11. This tends to provide that the minerals would exhibit the correct surface charge.

A conventional depressing agent, such as a hydrophilic polysaccharide, may be used in a conventional quantity sufficient to cover the iron or surface in the requisite amount. Typically a suitable hydrophilic polysaccharide includes different kinds of starches.

It may also be desirable to include a froth regulator in the system in order to improve the efficiency. Nevertheless such froth regulators are not essential. Examples of conventional from regulators include methylisobutyl carbinol and alcohols having between 6 and 12 carbon atoms, such as ethylhexanol, and alkoxylated alcohols.

Further conventional additives may be included in the flotation system, such as pH regulating agents, co-collectors, and extender oils.

The typical ores of iron suitable for treatment according to the invention include haematite and magnetite ores. The invention is particularly suitable to haematite. Furthermore, the invention is suitable for processing of iron ores, for instance haematites containing high silica contents, for instance at least 20% by weight of iron ore, often at least 30%, and even at least 40% or more, for instance up to 60% or 70% or more.

The present invention is further illustrated by the following examples.

EXAMPLES

Synthesis

Following alcohols have been transformed into corresponding alkyl ether amines by conversion with acrylonitrile and reduction of nitrile group to amino group. Compounds were optionally treated with acetic acid afterwards. Alkyl ether diamines have been produced from corresponding alkyl ether amines by conversion with acrylonitrile and reduction of nitrile group to amino group. Compounds were optionally treated with acetic acid afterwards.

TABLE 1

| Alcohol | Description |
| --- | --- |
| nC10 | n-C10H21OH, linear alcohol purchased by Aldrich (branching degree 0), not scope of the invention |
| C10-Guerbet | $C_5H_{11}CH(C_3H_7)CH_2OH$ with the restriction that for 70-99 weight % of compound $C_5H_{11}$ means n-$C_5H_{11}$ and for 1-30 weight % $C_5H_{11}$ means $C_2H_5CH(CH_3)CH_2$ and/or $CH_3CH(CH_3)CH_2CH_2$. Produced by BASF via dimerization of slightly branched C5-aldehyde via aldol reaction followed by hydrogenation. |
| C13C15 | C13C15 oxo-alcohol from BASF, produced by hydroformylation of C12C14-alpha-olefin, primary alcohol with average branching degree ranging from 0.3 to 0.7 |
| C12C14 | linear fatty alcohol with 12 and 14 carbon atoms |
| THV | Tetrahydrolavandulol, 2-Isopropyl-5-methylhexan-1-ol (Guerbet-alcohol with branching degree 3) |

To illustrate synthesis route the examples employ conversion of alcohol mixture ROH 50 weight % C10-Guerbet/ 50 weight % C13C15.

Synthesis of C10-Guerbet/C13C15 ether amine a) Addition

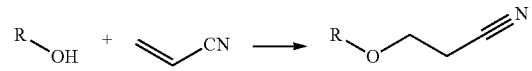

In a 1l round bottom flask C10-Guerbet alcohol (159 g, 1.0 mol) and C13C15 alcohol (159 g, 0.75 mol) were stirred with NaOMe (30% solution in MeOH, 2.62 g, 0.015 mol at 21° C. Acrylonitrile (186 g, 3.5 mol) was added during 45 min in such a way that temperature was kept below 50° C. Reaction was stirred overnight. Excess of acrylonitrile was removed under vacuum (20 mbar) at 50° C. (and later at 75° C.) within 30 min. Ambosol (3 weight %) was added and mixture was filtrated (900 k Seitz filter).

According to gas chromatogram (GC) mixture contains 1% alcohol and 99% addition product. Proton NMR (proton nmr in $CDCl_3$: δ=0.85-1.70, m, 22.4; H (CH, CH2, CH3), δ=2.6, t, 2H (CH2CN), δ=3.2-3.5, m, 2H (CH2O), δ=3.6, m, 2H (CH2O)) confirmed the structure.

b) Reduction

In a 300 ml autoclave tetrahydrofuran (35 g) was stirred with Raney-Cobalt (3.6 g) was flushed 3 times with nitrogen and stirred (500 rpm). Hydrogen (16.4 l) was added until pressure reached 50 bar and reactor was heated to 120° C. Product from addition step of C10-Guerbet/C13C15 and acrylonitrile (120 g, 0.51 mol) was added continuously (flow rate 1 ml/min). Pressure was increased to 60 bar. Additional hydrogen was added (17.7 l) until pressure of 280 bar was reached. Mixture was stirred for 6 h under these conditions. Pressure was kept at 280 bar (19.72 l were added). Reactor was cooled to room temperature and pressure gently released. Autoclave was flushed with nitrogen (10 bar). Catalyst was removed by filtration (Seitz K 900). According to amine titer, GC and proton NMR (proton nmr in CDCl$_3$: δ=0.8-1.7, m, 22.4; H (CH, CH2, CH3), δ=1.72, t, 2H (CH2), δ=2.8, t, 2H (CH2), δ=3.15-3.4, m, 2H (CH2O), δ=3.5, m, 2H (CH2O)) following values were achieved:

- 1.5% un-reacted nitrile
- 2.5% alcohol
- 94% alkyl ether amine
- 1.5% side-product ("dimer").

c) Partial Protonation

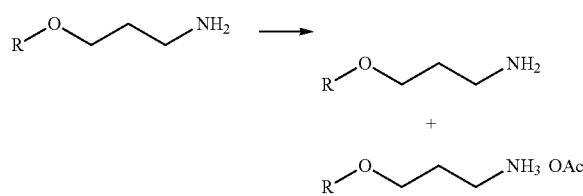

C10-Guerbet/C13C15-oxypropylamine (12 g, 0.050 mol) was stirred in a flask at room temperature. Acetic acid (0.6 g, 0.010 mol) was added drop-wise and stirred for 10 min. A homogeneous solution was observed, which stayed clear and liquid during storage for >3 months.

Synthesis of C10-Guerbet/C13C15 ether diamine a) Addition

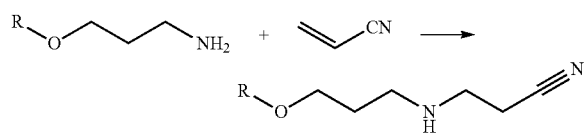

C10-Guerbet/C13C15-oxypropylamine (270 g, 1.08 mol) was stirred in a round bottom flask at 21° C. Acrylonitrile (63 g, 1.19 mol) was added during 15 min in such a way that temperature was kept below 50° C. Reaction was stirred for 3 h. Excess of acrylonitrile was removed under vacuum (20 mbar) at 50° C. (and later at 75° C.) within 30 min. According to amine titer, GC and proton NMR (proton nmr in CDCl$_3$: δ=0.8-1.70, m, 22.4H (CH, CH2, CH3), δ=1.75, t, (CH2), δ=2.5, t, (CH2CN), δ=2.75, t, (CH2), δ=2.95, t, (CH2), δ=3.15-3.4, m, (CH2O), δ=3.5, m, (CH2O)) following values were achieved:

- 2.7% alcohol
- 2.7% unreacted alkyl ether amin
- 7.6% side product
- 87% desired adduct.

b) Reduction

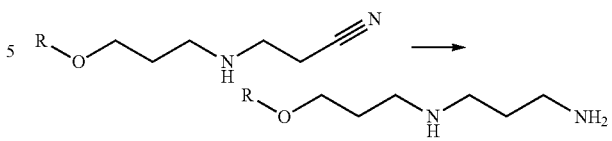

In an autoclave tetrahydrofuran (110 g) was stirred with Raney-Cobalt (13 g) was flushed 3 times with nitrogen and stirred (500 rpm). Hydrogen (123.7 l) was added until pressure reached 50 bar and reactor was heated to 120° C. Addition product of acrylonitrile and C10-Guerbet/C13C15-oxypropylamine (323 g, 1.109 mol) was added continuously (flow rate 6 ml/min). Pressure increased to 68 bar. Additional hydrogen was added until pressure of 280 bar was reached. Mixture was stirred for 6 h under these conditions. Pressure was kept at 280 bar (2.47 l were added). Reactor was cooled to room temperature and pressure gently released. Autoclave was flushed with nitrogen (10 bar). Catalyst was removed by filtration (Seitz K 900). According to amine titer, GC and proton NMR (proton nmr in CDCl$_3$: δ=0.85-1.60, m, 22.4H (CH, CH2, CH3), δ=1.65, q, (CH2), δ=1.75, t, (CH2), δ=2.70, m, (CH2), δ=2.75, t, (CH2), δ=3.15-3.4, m, (CH2O), δ=3.45, t, (CH2O)) following values were achieved:

- 4% alcohol
- 5.5% alkyl ether amine
- 84.5% alkyl ether diamine
- 6% side-product.

c) Partial Protonation

C10-Guerbet/C13C15-oxypropyl-1,3-propandiamine (80 g, 0.27 mol) was stirred in a flask at room temperature. Acetic acid (0.8 g, 0.0135 mol) was added drop-wise and stirred for 10 min. A homogeneous solution was observed, which stayed clear and liquid during storage for >3 months.

The other samples were produced in similar way like C10-Guerbet/C13C15-oxypropylamine or C10-Guerbet/C13C15-oxypropyl-1,3-propandiamine.

Flotation Test

Following flotation protocol was applied for the different collectors.

500 g of dried iron ore (hematite) were poured in a 1 l flotation vessel of a lab flotation cell (MN 935/5, HUMBOLDT WEDAG). 1 l tap water was added and the resulting slurry was homogenized by stirring for two minutes (3000 rpm). 25 mL of a 1 weight % freshly prepared corn starch solution (=500 g/t ore) were mixed in. Subsequently, 25 μL of the liquid collector were injected (=50 g/t ore), pH was adjusted to 10 (with 50 weight-% NaOH solution) and the slurry was conditioned for 5 minutes. The air flow was started (80 L/h) and the froth was collected until no stable froth was formed. The air flow was stopped and another 25 μL of collector were added and conditioned for 5 minutes, before the air flow was restarted. This procedure was repeated until five addition steps were carried out. The flotation froth of each step was dried, weighted and the obtained minerals characterized by elementary analysis via X-ray fluorescence (XRF).

It can be seen from the test work that the collectors according to the invention provide a better all-round combination of increased removal of silicate and increased retention of the iron mineral.

TABLE 2

|  |  | pH | weight g | weight % | Fe | Fe$_{rec.}$ | Fe$_{rec}$ (Residue) | Si | SiO$_2$ | SiO$_2$ (Residue) | SiO$_2$ $_{rec.}$ |
|---|---|---|---|---|---|---|---|---|---|---|---|
| Flotigam EDA | Froth 1 | 10.6 | 2 | 0.4% | 7.2% | 0.1% | 99.9% | 40.9% | 87.5% | 33.4% | 1.0% |
| iC12oxypropylamine + | Froth 2 | 10.4 | 3 | 0.6% | 7.2% | 0.1% | 99.8% | 40.9% | 87.5% | 33.1% | 1.5% |
| 50% acetic acid | Froth 3 | 10.3 | 10 | 2.0% | 7.2% | 0.3% | 99.5% | 40.9% | 87.5% | 32.0% | 5.2% |
| (Comparative | Froth 4 | 10.3 | 21 | 4.2% | 4.2% | 0.4% | 99.1% | 43.4% | 92.8% | 29.2% | 11.5% |
| monoamine) | Froth 5 | 10.2 | 22 | 4.4% | 3.9% | 0.4% | 98.8% | 43.4% | 92.8% | 26.1% | 12.0% |
|  | Residue | — | 447 | 88.5% | 50.4% | 98.8% |  | 12.2% | 26.1% |  | 68.7% |
|  | Total | — | 505 | 100.0% | 45.2% | 100.0% |  | 15.7% | 33.6% |  | 100.0% |
| Aerosurf MG-83 | Froth 1 | 10.6 | 8 | 1.6% | 12.4% | 0.4% | 99.6% | 36.9% | 78.9% | 34.3% | 3.6% |
| iC13oxypropyl-1,3- | Froth 2 | 10.4 | 6 | 1.2% | 17.0% | 0.5% | 99.1% | 33.5% | 71.7% | 33.8% | 2.4% |
| propan diamine + | Froth 3 | 10.3 | 14 | 2.8% | 16.4% | 1.0% | 98.1% | 34.3% | 73.4% | 32.6% | 5.8% |
| 5% acetic acid | Froth 4 | 9.8 | 55 | 10.9% | 4.7% | 1.1% | 96.9% | 42.9% | 91.8% | 24.9% | 28.6% |
| (Comparative | Froth 5 | 9.8 | 103 | 20.4% | 9.1% | 4.2% | 92.8% | 39.7% | 84.9% | 5.6% | 49.5% |
| diamine) | Residue | — | 319 | 63.2% | 65.4% | 92.8% |  | 2.6% | 5.6% |  | 10.0% |
|  | Total | — | 505 | 100.0% | 44.5% | 100.0% |  | 16.3% | 35.0% |  | 100.0% |
| Product 1 | Froth 1 | 10.2 | 9 | 1.8% | 6.5% | 0.2% | 99.8% | 40.9% | 87.5% | 31.7% | 4.8% |
| 1:1 (C10-Guerbetoxypropylamine + | Froth 2 | 10.2 | 41 | 8.1% | 6.5% | 1.1% | 98.6% | 41.5% | 88.8% | 26.6% | 22.0% |
| C 12/14- | Froth 3 | 9.9 | 50 | 9.9% | 3.6% | 0.8% | 97.9% | 43.7% | 93.5% | 18.3% | 28.3% |
| oxypropylamine) + | Froth 4 | 9.8 | 35 | 6.9% | 4.5% | 0.7% | 97.2% | 43.0% | 92.0% | 11.3% | 19.5% |
| 20% acetic acid | Froth 5 | 9.8 | 23 | 4.6% | 6.6% | 0.6% | 96.6% | 41.6% | 89.0% | 6.2% | 12.4% |
|  | Residue | — | 347 | 68.7% | 66.5% | 96.6% |  | 2.9% | 6.2% |  | 13.0% |
|  | Total | — | 505 | 100.0% | 47.3% | 100.0% |  | 15.3% | 32.7% |  | 100.0% |
| Product 2 | Froth 1 | 10.4 | 0 | 0.0% | 0.0% | 0.0% | 100.0% | 0.0% | 0.0% | 33.7% | 0.0% |
| 1:1 (C10-Guerbetoxypropylamine + | Froth 2 | 10.4 | 25 | 5.0% | 4.5% | 0.5% | 99.5% | 43.0% | 92.0% | 30.7% | 13.6% |
| C 13/15- | Froth 3 | 10.4 | 64 | 12.8% | 4.3% | 1.2% | 98.3% | 43.3% | 92.6% | 21.0% | 35.1% |
| oxypropylamine) + | Froth 4 | 9.9 | 50 | 10.0% | 3.7% | 0.8% | 97.5% | 43.8% | 93.7% | 11.0% | 27.7% |
| 5% acetic acid | Froth 5 | 9.9 | 22 | 4.4% | 7.4% | 0.7% | 96.8% | 41.3% | 88.3% | 6.0% | 11.5% |
|  | Residue | — | 340 | 67.9% | 65.3% | 96.8% |  | 2.8% | 6.0% |  | 12.1% |
|  | Total | — | 501 | 100.0% | 45.8% | 100.0% |  | 15.8% | 33.7% |  | 100.0% |

As one can see in table 2 commercial available Flotigam EDA used in example lead after 5 times flotation of iron ore to a residue still containing a relative high content of SiO2 (26.1%). In order to receive lower values of SiO2 in a residue after 5 times flotation one would need the more selective but also much more expensive and more complex alkyl ether diamines Aerosurf MG 83.

Surprisingly it was found that a combination of claimed compounds similar level of SiO$_2$ to the Aerosurf MG 83 can be reached. In case of product 2 a SiO$_2$ residual content of 6.0% was reached. The residual silica content is similar to that of Aerosurf MG 83 (5.6% SiO2), but the recovery rate of precious Fe was much higher for the inventive product (residue: 96.8% Fe compared to residue 92.8% Fe, for the Aerosurf MG 83). The advantage of the claimed combinations of alkyl ether amines is that one has a liquid sample, which is capable to reach similar low level of SiO2 level in treated ore, while loss of Fe is much lower compared to much more expensive and more complex to produce alkyl ether diamines.

TABLE 3

|  |  | pH | weight g | weight % | Fe | Ferec. | Frec (Residue) | Si | SiO2 | SiO2 (Residue) | SiO2 rec. |
|---|---|---|---|---|---|---|---|---|---|---|---|
| nC10oxypropylamine + | Froth 1 | 10.6 | 0 | 0.0% | 0.0% | 0.0% | 100.0% | 0.0% | 0.0% | 33.2% | 0.0% |
| 50 mol % acetic acid | Froth 2 | 10.6 | 21 | 4.2% | 5.7% | 0.5% | 99.5% | 41.9% | 89.6% | 30.8% | 11.3% |
|  | Froth 3 | 10.5 | 23 | 4.6% | 4.0% | 0.4% | 99.1% | 43.2% | 92.4% | 27.7% | 12.7% |
|  | Froth 4 | 10.5 | 26 | 5.2% | 4.5% | 0.5% | 98.6% | 43.2% | 92.4% | 23.8% | 14.4% |
|  | Froth 5 | 10.3 | 25 | 5.0% | 5.6% | 0.6% | 98.0% | 42.2% | 90.3% | 19.7% | 13.5% |
|  | Residue | — | 407 | 81.1% | 55.2% | 98.0% |  | 9.2% | 19.7% |  | 48.0% |
|  | Total | — | 502 | 100.0% | 45.7% | 100.0% |  | 15.5% | 33.2% |  | 100.0% |
| C10- | Froth 1 | 10.2 | 0 | 0.0% | 0.0% | 0.0% | 100.0% | 0.0% | 0.0% | 33.4% | 0.0% |
| Guerbetoxypropylamine + | Froth 2 | 10.1 | 0 | 0.0% | 0.0% | 0.0% | 100.0% | 0.0% | 0.0% | 33.4% | 0.0% |
| 50 mol % acetic acid | Froth 3 | 10.1 | 0 | 0.0% | 0.0% | 0.0% | 100.0% | 0.0% | 0.0% | 33.4% | 0.0% |
|  | Froth 4 | 10.1 | 33 | 6.6% | 2.2% | 0.3% | 99.7% | 44.7% | 95.6% | 29.0% | 18.9% |
|  | Froth 5 | 10.1 | 21 | 4.2% | 2.1% | 0.2% | 99.5% | 44.8% | 95.8% | 25.9% | 12.1% |
|  | Residue | — | 445 | 89.2% | 50.4% | 99.5% |  | 12.1% | 25.9% |  | 69.0% |
|  | Total | — | 499 | 100.0% | 45.2% | 100.0% |  | 15.6% | 33.4% |  | 100.0% |
| THVoxypropylamine + | Froth 1 | 10.4 | 0 | 0.0% | 0.0% | 0.0% | 100.0% | 0.0% | 0.0% | 30.0% | 0.0% |
| 50 mol % acetic acid | Froth 2 | 10.4 | 0 | 0.0% | 0.0% | 0.0% | 100.0% | 0.0% | 0.0% | 30.0% | 0.0% |
|  | Froth 3 | 10.3 | 0 | 0.0% | 0.0% | 0.0% | 100.0% | 0.0% | 0.0% | 30.0% | 0.0% |

TABLE 3-continued

| | pH | weight g | weight % | Fe | Ferec. | Frec (Residue) | Si | SiO2 | SiO2 (Residue) | SiO2 rec. |
|---|---|---|---|---|---|---|---|---|---|---|
| Froth 4 | 10.3 | 13 | 2.6% | 2.5% | 0.1% | 99.9% | 44.7% | 95.6% | 28.3% | 8.2% |
| Froth 5 | 10.2 | 8 | 1.6% | 2.6% | 0.1% | 99.8% | 44.8% | 95.8% | 27.2% | 5.1% |
| Residue | — | 481 | 95.8% | 49.3% | 99.8% | | 12.7% | 27.2% | | 86.7% |
| Total | — | 502 | 100.0% | 47.3% | 100.0% | | 14.0% | 30.0% | | 100.0% |

As one can see in table 3 C10-based alkyl ether amines can be used in general to remove larger parts of SiO2 within a precleaning step. In this step removal of significant loss of SiO2 is the goal at almost no loss of precious Fe. Collector based on linear C10-alcohol has two disadvantages. First of all it is solid. One needs a separate heating unit to keep it liquid for easy dosage. Second disadvantage can be seen in FE3-AH 182. While final SiO2 level in precleaning step is much lower compared to the other examples in table 3, loss of Fe is highest (2%). In case of the claimed compounds the loss of Fe is much lower (0.5% Fe max).

The invention claimed is:

1. A process for enriching an iron mineral from a silicate-containing iron ore, the process comprising:
performing inverse flotation by adding, to the silicate-containing iron ore, a collector or collector composition comprising at least one selected from the group consisting of compounds of formulae:

RO—X—NH$_2$ (Ia);

RO—X—NH$_3^+$Y$^-$ (Ib);

RO—X—NH—Z—NH$_2$ (IIa); and

RO—X—NH—Z—NH$_3^+$Y$^-$ (IIb), wherein
X is a linear or branched aliphatic alkylene group containing 2 to 6 carbon atoms;
Z is a linear or branched aliphatic alkylene group containing 2 to 6 carbon atoms;
Y$^-$ is an anion; and
R is an aliphatic group of formula (I):

C$_5$H$_{11}$CH(C$_3$H$_7$)CH$_2$— (I)

wherein the C$_5$H$_{11}$ moiety of the aliphatic group of the formula (I) comprises:
from 70 to 99% by weight of n-C$_5$H$_{11}$—, and
from 1 to 30% by weight of C$_2$H$_5$CH(CH$_3$)CH$_2$— and/or CH$_3$CH(CH$_3$)CH$_2$CH$_2$—.

2. The process according to claim 1,
wherein a C$_3$H$_7$ moiety of formula (I) is n-C$_3$H$_7$.

3. The process according to claim 1, wherein the collector or collector composition further comprises at least one selected from the group consisting of compounds of formulae:

R'O—X—NH$_2$ (Ic);

R'O—X—NH$_3^+$Y$^-$ (Id);

R'O—X—NH—Z—NH$_2$ (IIc); and

R'O—X—NH—Z—NH$_3^+$Y$^-$ (IId), wherein
X is a linear or branched aliphatic alkylene group containing 2 to 6 carbon atoms;
Z is a linear or branched aliphatic alkylene group containing 2 to 6 carbon atoms;
Y$^-$ is an anion;
and
R' is an aliphatic C$_{13}$H$_{27}$— group and/or an aliphatic C$_{15}$H$_{31}$— group each with an average branching degree ranging from 0.1 to 0.9.

4. The process according to claim 1,
wherein the collector or collector composition further comprises: at least one selected from the group consisting of compounds of formulae:

R"O—X—NH$_2$ (Ie);

R"O—X—NH$_3^+$Y$^-$ (If);

R"O—X—NH—Z—NH$_2$ (IIe); and

R"O—X—NH—Z—NH$_3^+$Y$^-$ (IIf), wherein
X is a linear or branched aliphatic alkylene group containing 2 to 6 carbon atoms;
Z is a linear or branched aliphatic alkylene group containing 2 to 6 carbon atoms;
Y$^-$ is an anion; and
R" is a linear aliphatic C$_{12}$H$_{25}$— group and/or a linear aliphatic C$_{14}$H$_{29}$— group.

5. The process according to claim 1,
wherein at least one of X and Z is an —CH$_2$CH$_2$CH$_2$— moiety.

6. The process according to claim 1,
wherein Y$^-$ is CH$_3$CO$_2^-$.

7. The process according to claim 1, further comprising performing froth flotation.

8. The process according to claim 1, further comprising employing an additional frother.

9. The process according to claim 1,
wherein the iron ore is haematite.

10. The process according to claim 1, further comprising adding a depressant.

11. The process according to claim 1, wherein the collector or the collector composition comprises at least one selected from the group consisting of compounds of formulae:

RO—X—NH$_2$ (Ia);

RO—X—NH$_3^+$Y$^-$ (Ib).

12. The process according to claim 1, wherein R is an aliphatic Guerbet C$_{10}$H$_{21}$— group with an average degree of branching of between 1.01 and 1.60.

* * * * *